(12) United States Patent
Park et al.

(10) Patent No.: US 8,445,119 B2
(45) Date of Patent: *May 21, 2013

(54) CHARGE TRANSPORT MATERIALS FOR LUMINESCENT APPLICATIONS

(75) Inventors: Kyung-Ho Park, Wilmington, DE (US); William J. Delaney, Bear, DE (US)

(73) Assignee: EI du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/402,345

(22) Filed: Feb. 22, 2012

(65) Prior Publication Data

US 2012/0146015 A1    Jun. 14, 2012

Related U.S. Application Data

(63) Continuation of application No. 12/336,801, filed on Dec. 17, 2008, now Pat. No. 8,174,185.

(60) Provisional application No. 61/015,815, filed on Dec. 21, 2007.

(51) Int. Cl.
*H01L 51/54* (2006.01)
*C07D 231/56* (2006.01)

(52) U.S. Cl.
USPC ............. 428/690; 257/40; 548/361.1; 585/26

(58) Field of Classification Search
None
See application file for complete search history.

(56) References Cited

U.S. PATENT DOCUMENTS

| | | |
|---|---|---|
| 6,303,238 B1 | 10/2001 | Thompson et al. |
| 6,670,645 B2 | 12/2003 | Grushin et al. |
| 6,713,192 B2 | 3/2004 | Fukuoka et al. |

(Continued)

FOREIGN PATENT DOCUMENTS

| | | |
|---|---|---|
| JP | 02007066 A * | 1/1990 |
| WO | 0070655 A2 | 11/2000 |

(Continued)

OTHER PUBLICATIONS

English language translation of JP 02007066 A.*

(Continued)

*Primary Examiner* — Jennifer Chriss
*Assistant Examiner* — J. L. Yang

(57) ABSTRACT

There is provided a charge transport compound having Formula I:

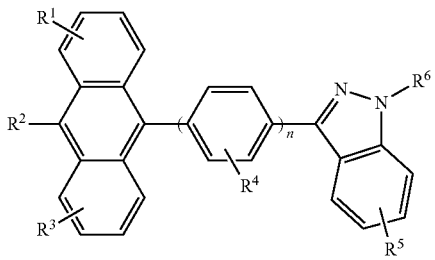

Formula I wherein:
 $R^1$ through $R^5$ are the same or different at each occurrence and can be hydrogen, alkyl, aryl, halogen, hydroxyl, aryloxy, alkoxy, alkenyl, alkynyl, amino, alkylthio, phosphino, silyl, —COR, —COOR, —PO$_3$R$_2$, —OPO$_3$R$_2$, or CN;
 $R^6$ can be hydrogen, alkyl, aryl, alkylaryl, and arylalkyl;
 R is the same or different at each occurrence and can be hydrogen, alkyl, aryl, alkenyl, and alkynyl; and
 n is an integer from 0-3.

11 Claims, 1 Drawing Sheet

U.S. PATENT DOCUMENTS

| | | | |
|---|---|---|---|
| 7,361,796 B2 | 4/2008 | Ikeda et al. | |
| 8,174,185 B2 * | 5/2012 | Park et al. | 313/504 |
| 2004/0102577 A1 | 5/2004 | Hsu et al. | |
| 2004/0127637 A1 | 7/2004 | Hsu et al. | |
| 2005/0205860 A1 | 9/2005 | Hsu et al. | |
| 2006/0043858 A1 | 3/2006 | Ikeda et al. | |
| 2006/0154076 A1 | 7/2006 | Kubota et al. | |
| 2007/0020540 A1 | 1/2007 | Qi et al. | |
| 2007/0088185 A1 | 4/2007 | Kubota et al. | |
| 2007/0152565 A1 | 7/2007 | Kubota et al. | |
| 2007/0172698 A1 * | 7/2007 | Iwakuma et al. | 428/690 |

FOREIGN PATENT DOCUMENTS

| | | |
|---|---|---|
| WO | 0141512 A1 | 6/2001 |
| WO | 03008424 A1 | 1/2003 |
| WO | 03040257 A1 | 5/2003 |
| WO | 03063555 A1 | 7/2003 |
| WO | 03091688 A2 | 11/2003 |
| WO | 2004016710 A1 | 2/2004 |
| WO | WO 2005/084083 A1 * | 9/2005 |

OTHER PUBLICATIONS

Gustafsson et al., Flexible Light-Emitting Diodes Made from Soluble Conducting Polymer, Nature, vol. 357. pp. 477-479 (Jun. 11, 1992).

Wang—Photoconductive Materials, Kirk-Othmer Encyclopedia of Chemical Technology, Fourth Edition, 1996, vol. 18, pp. 837-860.

Markus et al—Electronics and Nuleonics Dictionary, pp. 470 & 476 (McGraw-Hill 1966) (Book not Included).

Fujii et al., "An Organic Infrared Electroluminescent Diode Utilizing a Phthalocyanine Film," IEEE Transactions on Electron Devices, vol. 44, 1997, pp. 1204-1207.

* cited by examiner

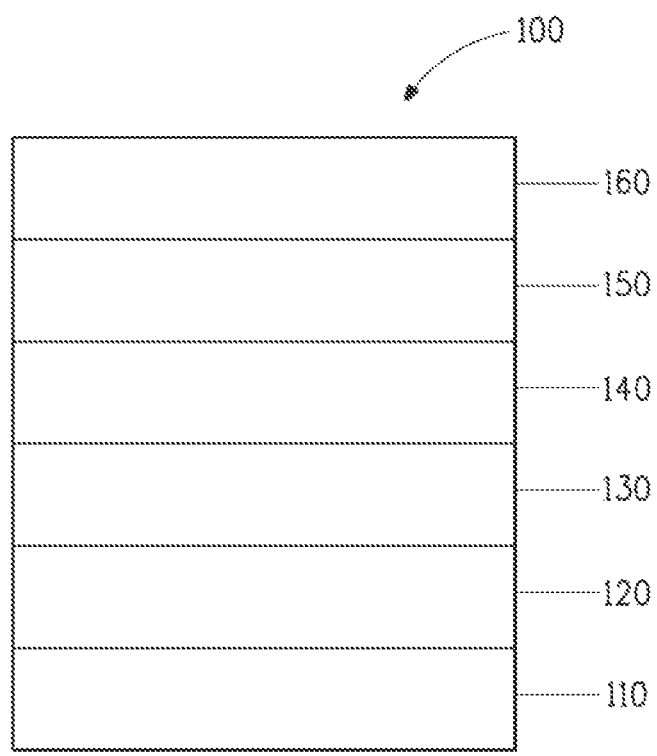

CHARGE TRANSPORT MATERIALS FOR LUMINESCENT APPLICATIONS

RELATED APPLICATION

This application claims priority under 35 U.S.C. §120 from U.S. patent application Ser. No. 13/336,801, filed Dec. 17, 2008 (incorporated by reference herein in its entirety), which in turn claimed priority under 35 U.S.C. §119(e) from Provisional Application No. 61/015,815 filed on Dec. 21, 2007 which is incorporated by reference in its entirety.

BACKGROUND INFORMATION

1. Field of the Disclosure

This disclosure relates in general to charge transport materials that can be used in luminescent applications. In particular, the materials can be used as hosts for light-emitting materials. The disclosure further relates to electronic devices having at least one active layer comprising such a charge transport material.

2. Description of the Related Art

In organic photoactive electronic devices, such as organic light emitting diodes ("OLED"), that make up OLED displays, the organic active layer is sandwiched between two electrical contact layers in an OLED display. In an OLED, the organic photoactive layer emits light through the light-transmitting electrical contact layer upon application of a voltage across the electrical contact layers.

It is well known to use organic electroluminescent compounds as the active component in light-emitting diodes. Simple organic molecules, conjugated polymers, and organometallic complexes have been used. Devices that use photoactive materials frequently include one or more charge transport layers, which are positioned between a photoactive (e.g., light-emitting) layer and a contact layer (hole-injecting contact layer). A device can contain two or more contact layers. A hole transport layer can be positioned between the photoactive layer and the hole-injecting contact layer. The hole-injecting contact layer may also be called the anode. An electron transport layer can be positioned between the photoactive layer and the electron-injecting contact layer. The electron-injecting contact layer may also be called the cathode. Charge transport materials can also be used as hosts in combination with the photoactive materials.

There is a continuing need for charge transport materials for use in electronic devices.

SUMMARY OF THE DISCLOSURE

There is provided a compound having Formula I:

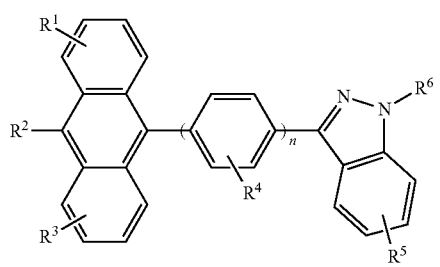

Formula I wherein:
$R^1$ through $R^5$ are the same or different at each occurrence and are independently selected from the group consisting of hydrogen, alkyl, aryl, halogen, hydroxyl, aryloxy, alkoxy, alkenyl, alkynyl, amino, alkylthio, phosphino, silyl, —COR, —COOK, —PO$_3$R$_2$, —OPO$_3$R$_2$, and CN;

$R^6$ is selected from the group consisting of hydrogen, alkyl, aryl, alkylaryl, and arylalkyl;

R is the same or different at each occurrence and is independently selected from the group consisting of hydrogen, alkyl, aryl, alkenyl, and alkynyl; and n is an integer from 0-3.

There is also provided an electronic device comprising at least one layer comprising the above compound.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

FIG. 1 includes an illustration of one example of an organic electronic device.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Many aspects and embodiments are described herein and are merely exemplary and not limiting. After reading this specification, skilled artisans will appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Charge Transport Materials, the Electronic Device, and finally Examples.

1. Definitions and Clarification of Terms

Before addressing details of embodiments described below, some terms are defined or clarified.

The phrase "adjacent to," when used to refer to layers in a device, does not necessarily mean that one layer is immediately next to another layer. On the other hand, the phrase "adjacent R groups," is used to refer to R groups that are next to each other in a chemical formula (I.e., R groups that are on atoms joined by a bond).

The term "alkenyl" is intended to mean a group derived from an aliphatic hydrocarbon having at least one carbon-carbon double bond. The term is intended to include heteroalkyl groups.

The term "alkoxy" is intended to mean a group having the formula —OR, which is attached via the oxygen, where R is an alkyl.

The term "alkyl" is intended to mean a group derived from an aliphatic hydrocarbon having one point of attachment, and includes a linear, a branched, or a cyclic group. The term is intended to include heteroalkyls. The term "alkylene" is intended to mean a group derived from an aliphatic hydrocarbon and having two or more points of attachment. In some embodiments, an alkyl group has from 1-20 carbon atoms. In some embodiments, the heteroalkyl groups have from 1-20 carbon atoms and from 1-5 heteroatoms.

The term "alkylthio" is intended to mean a group having the formula —SR, which is attached via the sulfur, where R is an alkyl.

The term "alkynyl" is intended to mean a group derived from an aliphatic hydrocarbon having at least one carbon-carbon triple bond.

The term "aryl" is intended to mean a group derived from an aromatic hydrocarbon having one point of attachment. The term is intended to include heteroaryls. The term "arylene" is intended to mean a group derived from an aromatic hydrocarbon having two points of attachment. In some embodiments, an aryl group has from 3-60 carbon atoms.

The term "blue" refers to radiation that has an emission maximum at a wavelength in a range of approximately 400-500 nm.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport material facilitate negative charge. Although light-emitting materials may also have some charge transport properties, the term "charge transport layer, material, member, or structure" is not intended to include a layer, material, member, or structure whose primary function is light emission.

The prefix "fluoro" indicates that one or more hydrogen atoms have been replaced with a fluorine atom.

The prefix "hetero" indicates that one or more carbon atoms have been replaced with a different atom. In some embodiments, the different atom is N, O, or S.

The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating. Discontinuous deposition techniques include, but are not limited to, ink jet printing, gravure printing, and screen printing.

The term "organic electronic device," or sometimes just "electronic device," is intended to mean a device including one or more organic semiconductor layers or materials.

Unless otherwise indicated, all groups can be substituted or unsubstituted. An optionally substituted group, such as, but not limited to, alkyl or aryl, may be substituted with one or more substituents which may be the same or different. Suitable substituents include alkyl, aryl, nitro, cyano, —N($R^7$)($R^8$), halo, hydroxy, carboxy, alkenyl, alkynyl, cycloalkyl, heteroaryl, alkoxy, aryloxy, heteroaryloxy, alkoxycarbonyl, perfluoroalkyl, perfluoroalkoxy, arylalkyl, thioalkoxy, —S(O)$_2$—N(R')(R"), —C(=O)—N(R')(R"), (R')(R")N-alkyl, (R')(R")N-alkoxyalkyl, (R')(R")N-alkylaryloxyalkyl, —S(O)$_s$—aryl (where s=0-2) or —S(O)$_s$-heteroaryl (where s=0-2). Each R' and R" is independently an optionally substituted alkyl, cycloalkyl, or aryl group. R' and R", together with the nitrogen atom to which they are bound, can form a ring system in certain embodiments.

The term "photoactive" is intended to mean any material that exhibits electroluminescence or photosensitivity.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

2. Charge Transport Materials

The new compounds described herein are particularly useful as host materials for photoactive materials. The compounds have Formula I:

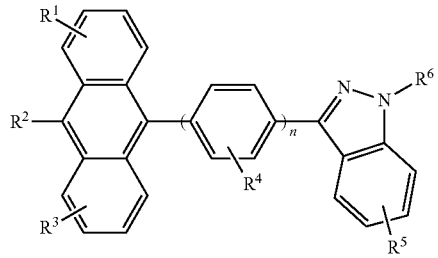

Formula I wherein:
R$^1$ through R$^5$ are the same or different at each occurrence and are independently selected from the group consisting of hydrogen, alkyl, aryl, halogen, hydroxyl, aryloxy, alkoxy, alkenyl, alkynyl, amino, alkylthio, phosphino, silyl, —COR, —COOR, —PO$_3$R$_2$, —OPO$_3$R$_2$, and CN;
R$^6$ is selected from the group consisting of hydrogen, alkyl, aryl, alkylaryl, and arylalkyl;

R is the same or different at each occurrence and is independently selected from the group consisting of hydrogen, alkyl, aryl, alkenyl, and alkynyl; and n is an integer from 0-3.

In Formula I, $R^1$, $R^3$, $R^4$, and $R^5$ can represent one or more substituents which can be the same or different. In some embodiments, $R^1$, $R^3$, $R^4$, and $R^5$ are independently selected from hydrogen, alkyl, alkoxy, and aryl. In some embodiments, $R^1$, $R^3$, $R^4$, and $R^5$ are all hydrogen.

In some embodiments, $R^2$ is an aryl group. In some embodiments, $R^2$ is selected from phenyl and naphthyl.

In some embodiments, $R^6$ is selected from the group consisting of alkyl, aryl, alkoxyl, and aryloxy. In some embodiments, $R^6$ is aryl. In some embodiments, $R^6$ is selected from phenyl and naphthyl. In some embodiments, $R^6$ is arylalkyl. In some embodiments, $R^6$ is alkyl. In some embodiments, $R^6$ is a branched alkyl.

In some embodiments, n is 0 or 1.

In some embodiments, the charge transport compound is selected from Compounds H1 through H5 below.

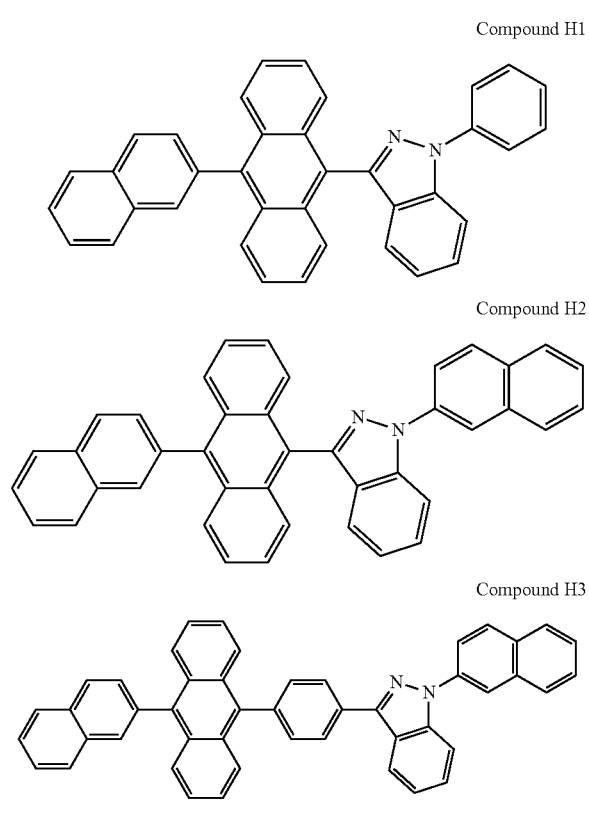

Compound H1

Compound H2

Compound H3

Compound H4

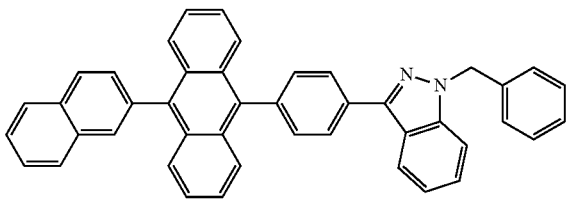

Compound H5

The new charge transport compounds can be prepared by known coupling and substitution reactions. One general synthetic route is shown below.

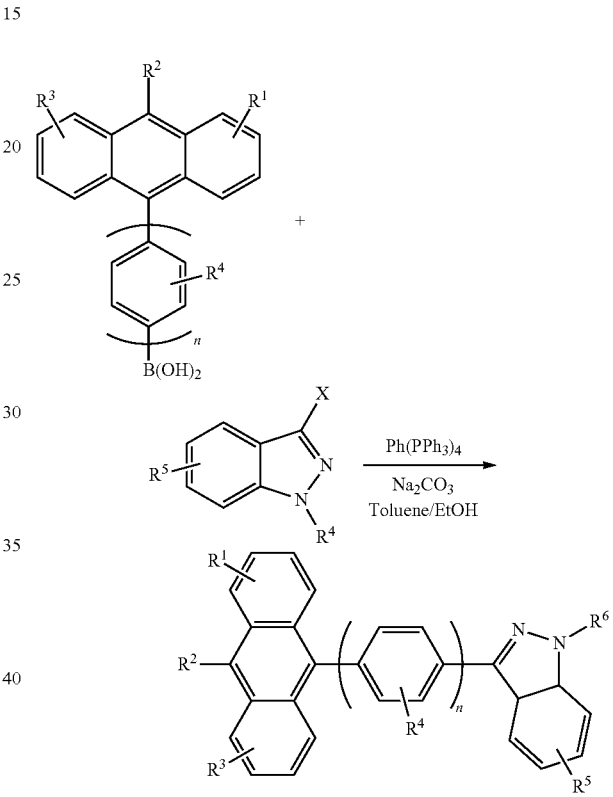

The synthesis is exemplified further in the examples.

The new compounds described herein can be formed into films using liquid deposition techniques.

3. Electronic Device

The present invention also relates to an electronic device comprising at least one photoactive layer positioned between two electrical contact layers, wherein the at least one layer of the device includes the new charge transport compound described herein.

Organic electronic devices that may benefit from having one or more layers comprising the new charge transport materials described herein include, but are not limited to, (1) devices that convert electrical energy into radiation (e.g., a light-emitting diode, light emitting diode display, or diode laser), (2) devices that detect signals through electronics processes (e.g., photodetectors, photoconductive cells, photoresistors, photoswitches, phototransistors, phototubes, IR detectors), (3) devices that convert radiation into electrical energy, (e.g., a photovoltaic device or solar cell), and (4) devices that include one or more electronic components that include one or more organic semi-conductor layers (e.g., a transistor or diode).

One illustration of an organic electronic device structure is shown in FIG. 1. The device 100 has a first electrical contact layer, an anode layer 110 and a second electrical contact layer, a cathode layer 160, and a photoactive layer 140 between them. Adjacent to the anode is a buffer layer 120. Adjacent to the buffer layer is a hole transport layer 130, comprising hole transport material. Adjacent to the cathode may be an electron transport layer 150, comprising an electron transport material. As an option, devices may use one or more additional hole injection or hole transport layers (not shown) next to the anode 110 and/or one or more additional electron injection or electron transport layers (not shown) next to the cathode 160.

Layers 120 through 150 are individually and collectively referred to as the active layers.

In one embodiment, the different layers have the following range of thicknesses: anode 110, 500-5000 Å, in one embodiment 1000-2000 Å; buffer layer 120, 50-2000 Å, in one embodiment 200-1000 Å; hole transport layer 130, 50-2000 Å, in one embodiment 200-1000 Å; photoactive layer 140, 10-2000 Å, in one embodiment 100-1000 Å; layer 150, 50-2000 Å, in one embodiment 100-1000 Å; cathode 160, 200-10000 Å, in one embodiment 300-5000 Å. The location of the electron-hole recombination zone in the device, and thus the emission spectrum of the device, can be affected by the relative thickness of each layer. The desired ratio of layer thicknesses will depend on the exact nature of the materials used.

Depending upon the application of the device 100, the photoactive layer 140 can be a light-emitting layer that is activated by an applied voltage (such as in a light-emitting diode or light-emitting electrochemical cell), or a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are described in Markus, John, *Electronics and Nucleonics Dictionary*, 470 and 476 (McGraw-Hill, Inc. 1966).

The charge transport compounds described herein can be present in the photoactive layer or in a charge transport layer.

a. Photoactive Layer

The charge transport compounds described herein are useful as hosts for the photoactive materials in layer 140.

The photoactive material can be any electroluminescent ("EL") material having the desired color. Electroluminescent materials include small molecule organic fluorescent compounds, fluorescent and phosphorescent metal complexes, conjugated polymers, and mixtures thereof. Examples of fluorescent compounds include, but are not limited to, pyrene, perylene, rubrene, coumarin, derivatives thereof, and mixtures thereof. Examples of metal complexes include, but are not limited to, metal chelated oxinoid compounds, such as tris(8-hydroxyquinolato)aluminum (Alq3); cyclometalated iridium and platinum electroluminescent compounds, such as complexes of iridium with phenylpyridine, phenylquinoline, or phenylpyrimidine ligands as disclosed in Petrov et al., U.S. Pat. No. 6,670,645 and Published PCT Applications WO 03/063555 and WO 2004/016710, and organometallic complexes described in, for example, Published PCT Applications WO 03/008424, WO 03/091688, and WO 03/040257, and mixtures thereof. Electroluminescent emissive layers comprising a charge carrying host material and a metal complex have been described by Thompson et al., in U.S. Pat. No. 6,303,238, and by Burrows and Thompson in published PCT applications WO 00/70655 and WO 01/41512. Examples of conjugated polymers include, but are not limited to poly (phenylenevinylenes), polyfluorenes, poly(spirobifluorenes), polythiophenes, poly(p-phenylenes), copolymers thereof, and mixtures thereof.

In some embodiments, the EL material is a cyclometalated complex of iridium. In some embodiments, the complex has two ligands selected from phenylpyridines, phenylquinolines, and phenylisoquinolines, and a third ligand with is a β-dienolate. The ligands may be unsubstituted or substituted with F, D, alkyl, CN, or aryl groups.

In some embodiments, the EL material is selected from the group consisting of a non-polymeric spirobifluorene compound and a fluoranthene compound.

In some embodiments, the EL material is a compound having aryl amine groups. In one embodiment, the EL material is selected from the formulae below:

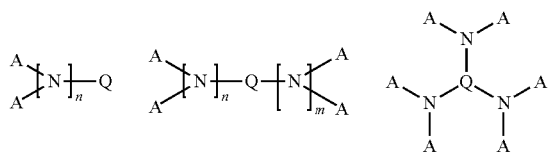

where:

A is the same or different at each occurrence and is an aromatic group having from 3-60 carbon atoms;

Q is a single bond or an aromatic group having from 3-60 carbon atoms;

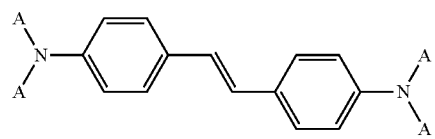

n and m are independently an integer from 1-6.

In one embodiment of the above formula, at least one of A and Q in each formula has at least three condensed rings. In one embodiment, m and n are equal to 1. In one embodiment, Q is a styryl or styrylphenyl group.

In some embodiments, Q is an aromatic group having at least two condensed rings. In some embodiments, Q is selected from the group consisting of naphthalene, anthracene, chrysene, pyrene, tetracene, xanthene, perylene, coumarin, rhodamine, quinacridone, and rubrene. In some embodiments, A is selected from the group consisting of phenyl, tolyl, naphthyl, and anthracenyl groups.

In one embodiment, the EL material has the formula below:

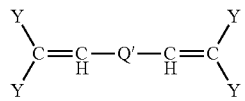

where:

Y is the same or different at each occurrence and is an aromatic group having 3-60 carbon atoms;

Q' is an aromatic group, a divalent triphenylamine residue group, or a single bond.

In some embodiments, the EL material is an aryl acene. In some embodiments, the EL material is a non-symmetrical aryl acene.

In some embodiments, the EL material is a chrysene derivative. The term "chrysene" is intended to mean 1,2-benzophenanthrene. In some embodiments, the EL material is a chrysene having aryl substituents. In some embodiments, the EL material is a chrysene having arylamino substituents. In some embodiments, the EL material is a chrysene having two different arylamino substituents.

In some embodiments, the EL material has blue or green emission.

In some embodiments, the ratio of host material to EL material is in the range of 5:1 to 20:1; in some embodiments, 10:1 to 15:1.

The new charge transport compounds described herein are particularly useful as hosts for fluorescent organic compounds, including aromatic and arylamino-aromatic compounds.

b. Other Device Layers

The other layers in the device can be made of any materials that are known to be useful in such layers.

The anode 110, is an electrode that is particularly efficient for injecting positive charge carriers. It can be made of, for example, materials containing a metal, mixed metal, alloy, metal oxide or mixed-metal oxide, or it can be a conducting polymer, or mixtures thereof. Suitable metals include the Group 11 metals, the metals in Groups 4-6, and the Group 8-10 transition metals. If the anode is to be light-transmitting, mixed-metal oxides of Groups 12, 13 and 14 metals, such as indium-tin-oxide, are generally used. The anode 110 can also comprise an organic material such as polyaniline as described in "Flexible light-emitting diodes made from soluble conducting polymer," Nature vol. 357, pp 477-479 (11 Jun. 1992). At least one of the anode and cathode is desirably at least partially transparent to allow the generated light to be observed.

The buffer layer 120 comprises buffer material and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. Buffer materials may be polymers, oligomers, or small molecules. They may be vapour deposited or deposited from liquids which may be in the form of solutions, dispersions, suspensions, emulsions, colloidal mixtures, or other compositions.

The buffer layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like.

The buffer layer can comprise charge transfer compounds, and the like, such as copper phthalocyanine and the tetrathiafulvalene-tetracyanoquinodimethane system (TTF-TCNQ).

In some embodiments, the buffer layer comprises at least one electrically conductive polymer and at least one fluorinated acid polymer. Such materials have been described in, for example, published U.S. Patent applications 2004-0102577, 2004-0127637, and 2005/205860

The compounds described herein can also be used as hole transport materials in hole transport layer 130. Examples of other hole transport materials for layer 130 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3[p-(diethylamino)styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), N,N'-bis(naphthalen-1-yl)-N,N'-bis-(phenyl)benzidine (α-N PB), and porphyrinic compounds, such as copper phthalocyanine. Commonly used hole transporting polymers are polyvinylcarbazole, (phenylmethyl)-polysilane, and polyaniline. It is also possible to obtain hole transporting polymers by doping hole transporting molecules such as those mentioned above into polymers such as polystyrene and polycarbonate. In some cases, a polymer of triarylamine is used, particularly a copolymer of triarylamine and fluorene. In some cases the polymer or copolymer is crosslinkable.

Examples of electron transport materials which can be used in layer 150 include metal chelated oxinoid compounds, such as tris(8-hydroxyquinolato)aluminum ($Alq_3$); bis(2-methyl-8-quinolinolato)(para-phenyl-phenolato)aluminum(III) (BAlQ); and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ), and 1,3,5-tri(phenyl-2-benzimidazole)benzene (TPBI); quinoxaline derivatives such as 2,3-bis(4-fluorophenyl)quinoxaline; phenanthroline derivatives such as 9,10-diphenylphenanthroline (DPA) and 2,9-dimethyl-4,7-diphenyl-1,10-phenanthroline (DDPA); and mixtures thereof. Layer 150 can function both to facilitate electron transport, and also serve as a buffer layer or confinement layer to prevent quenching of the exciton at layer interfaces. Preferably, this layer promotes electron mobility and reduces exciton quenching.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds, LiF, and $Li_2O$ can also be deposited between the organic layer and the cathode layer to lower the operating voltage.

It is known to have other layers in organic electronic devices. For example, there can be a layer (not shown) between the anode 110 and buffer layer 120 to control the amount of positive charge injected and/or to provide bandgap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, active layers 120, 130, 140, and 150, or cathode layer 160, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

The device can be prepared by a variety of techniques, including sequential vapor deposition of the individual layers on a suitable substrate. Substrates such as glass, plastics, and metals can be used. Conventional vapor deposition techniques can be used, such as thermal evaporation, chemical vapor deposition, and the like. Alternatively, the organic layers can be applied from solutions or dispersions in suitable solvents, using conventional coating or printing techniques, including but not limited to spin-coating, dip-coating, roll-to-roll techniques, ink-jet printing, screen-printing, gravure printing and the like. The new charge transport compounds described herein are particularly suited to liquid deposition processes for forming films.

Devices frequently have additional hole transport and electron transport layers.

It is understood that the efficiency of devices made with the compounds having Formula I described herein, can be further improved by optimizing the other layers in the device. For example, more efficient cathodes such as Ca, Ba or LiF can be used. Shaped substrates and novel hole transport materials that result in a reduction in operating voltage or increase quantum efficiency are also applicable. Additional layers can also be added to tailor the energy levels of the various layers and facilitate electroluminescence.

The concepts described herein will be further described in the following examples, which do not limit the scope of the invention described in the claims.

EXAMPLES

Example 1

This example illustrates the preparation of charge transport material Compound H1.

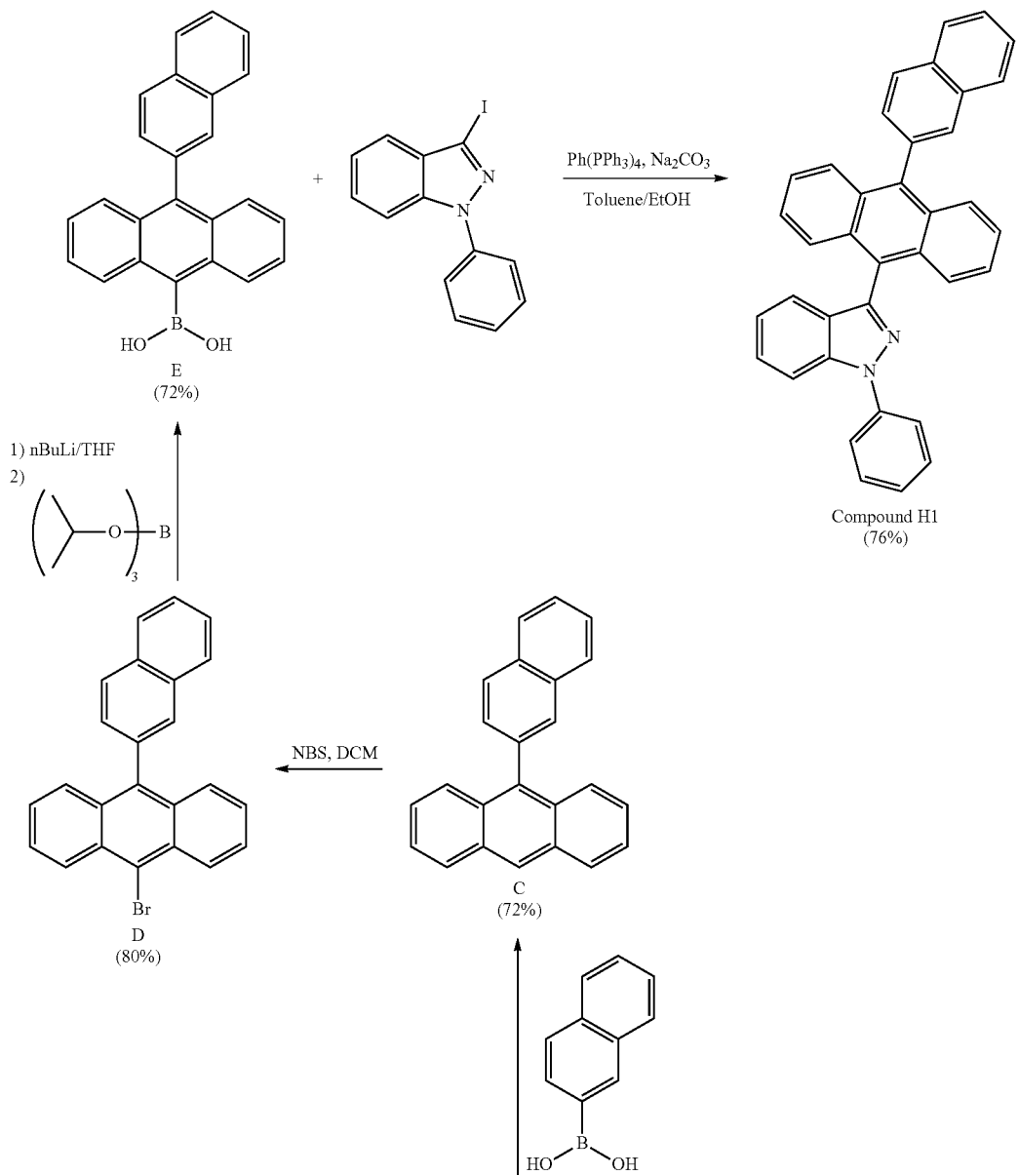

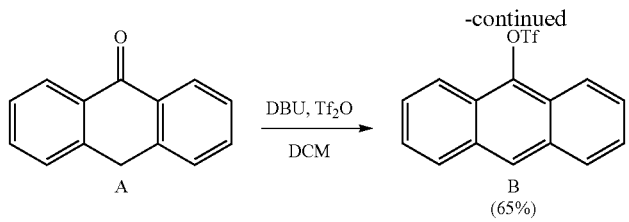

a. Preparation of Anthracene-9-triflate, intermediate B

In a 1 L flask was added anthrone (compound A, 54 g, 275.2 mmol) in 1.5 L dry methylene chloride. The flask was cooled in an ice bath and 83.7 mL DBU (559.7 mmol) was added dropwise over 1.5 hours under $N_2$. The solution turned orange, became opaque, then turned deep red. To the still cooled solution was added 58 mL trifluoromethanesulfonic anhydride (345 mmol) via syringe over about 1.5 hr by keeping the temperature of the solution below 5° C. When the reaction was almost complete after 3 hrs, 1 mL additional trifluoromethanesulfonic anhydride was added and the mixture was stirred for another 30 min. 500 mL of water was added and the layers were separated. The aqueous layer was washed with DCM (3×200 mL) and the combined organic layer was dried over magnesium sulfate, and then concentrated under reduced pressure to give a red oil. This red oil was passed through a silica gel (column solvent: hexane, then Hex/DCM=95/5) to provide a solid material. This material was recrystallized from hexane to yield 57.5 g (65%) of B as a white crystalline solid.

b. Preparation of 9-(Naphthalen-2-yl)-anthracene, intermediate C 3 g of compound B (1 eq), 1.9 g of naphthalene-2-yl-boronic acid (1.2 eq), 8.8 g of potassium phosphate tribasic (4.5 eq), 0.103 g of palladium (II) acetate (0.05 eq), and 0.129 g of tricyclohexylphosphine (0.05 eq) were combined in a 200 ml RB flask in the glove box, followed by the addition of 25 ml of toluene and 25 ml degassed water. The resultant mixture was refluxed for 20 hrs under $N_2$. After cooling the mixture to rt, the organic layer was separated and the aqueous layer was extracted with DCM (3×50 ml). The combined organic layer was washed with 100 ml brine, dried with $MgSO_4$, and concentrated under reduced pressure to a tan powder. By neutral alumina column chromatography using DCM as an eluent, 2.0 g of compound C (72%) was obtained as a solid.

c. Preparation of Intermediate D 9-(Naphthalen-2-yl)-anthracene, compound C, (30 g, 98.56 mmol) was suspended in 300 mL DCM, followed by the addition of NBS (18.4 g, 103.38 mmol) to the flask. The mixture was refluxed under $N_2$ by illuminating the reaction flask with 100 W lamp. After 1.5 h the reaction mixture was concentrated to the half of the total volume, then hot acetonitrile was added. The solution was allowed to cool to give a pale yellow solid. The crystal was filtered and washed with acetonitrile, providing 28.9 g of compound D (80%).

d. Preparation of Intermediate E

Into a solution of 9-bromo-10-naphthalen-2-yl-anthracene (compound D, 12.0 g, 1 eq) dissolved in anhydrous THF (200 mL), was added slowly n-BuLi (2.5 M in hexane, 12.4 mL, 1.2 eq) at −78° C. under $N_2$. The deep red reaction mixture was stirred for 2 hr. Triisopropylborate (5.89 g, 1.2 eq) was added dropwise into the cooled solution and stirred at this temperature for 0.5 h. The solution became bright yellow over this time. The reaction was warmed up to room temperature and stirred for 1 hr. After quenching the mixture with 20% HCl solution (100 mL) for 1 hr the organic layer was separated and the aqueous layer was extracted with EtOAc (3×100 mL). The combined organic layer was dried over anhydrous sodium sulfate, then concentrated under reduced pressure to a yellow solid. This solid was suspended in a small amount of EtOAc and the precipitated solid was filtered to give 7.8 g of compound E (72%).

e. Preparation of Compound H1

To the solution of 3-iodo-1-phenylindazole (1.1 g, 1eq) in toluene (30 mL) and ethanol (15 mL) were added 10-(2-naphthyl)-anthracene-9-boronic acid (compound E, 1.43 g, 1.2 eq), $Pd(PPh_3)_4$ (0.2 g, 0.05 eq), and $Na_2CO_3$ (2.18 g, 6 eq), followed by the addition of 25 ml of degassed water. The mixture was refluxed overnight under $N_2$, and then it was extracted with EtOAc (2×50 ml). The combined organic layer was washed with water, dried with $Na_2SO_4$, and concentrated under reduced pressure. By silica gel column chromatography (20% DCM/hexane, then 10% EtOAc/hexane) compound H1 (1.29 g, 76%) was obtained as a pale yellow solid.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

The use of numerical values in the various ranges specified herein is stated as approximations as though the minimum and maximum values within the stated ranges were both being preceded by the word "about." In this manner slight variations above and below the stated ranges can be used to achieve substantially the same results as values within the

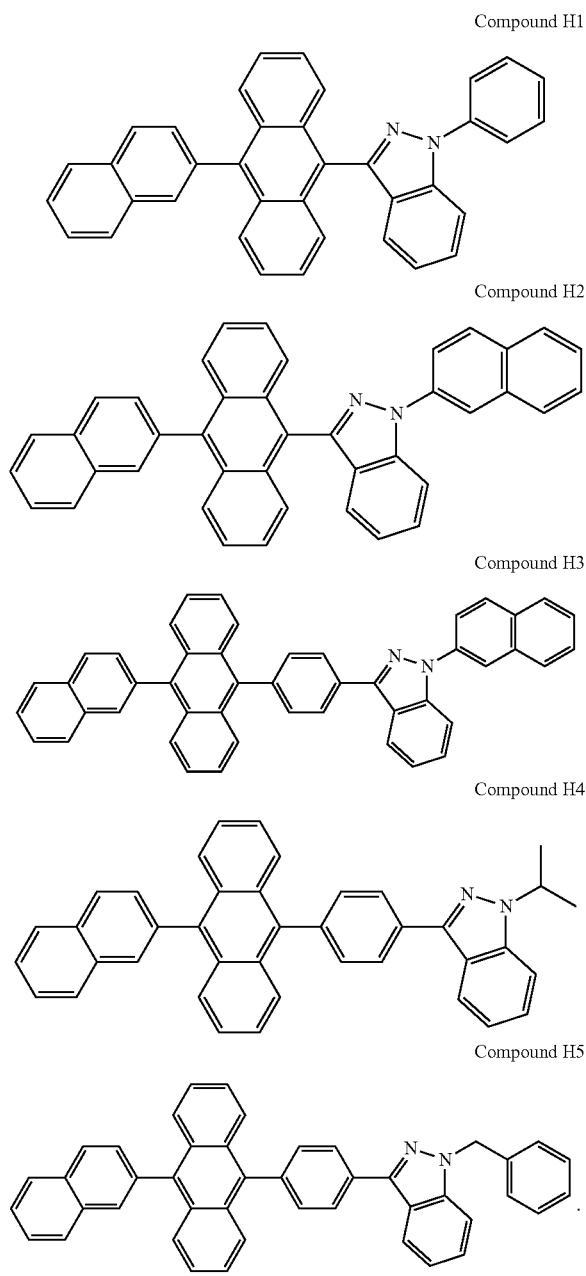

What is claimed is:

1. An organic electronic device selected from a light-emitting diode, a light-emitting electrochemical cell, and a photodetector, said device comprising an anode, a buffer layer, a hole transport layer, a photoactive layer, an electron transport layer, and cathode, wherein at least one layer positioned between the anode and the cathode comprises a compound having Formula I:

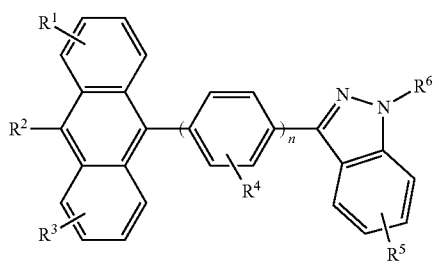

Formula I wherein:
R$^1$ and R$^3$ through R$^5$ are the same or different at each occurrence and are independently selected from the group consisting of hydrogen, alkyl, aryl, halogen, hydroxyl, aryloxy, alkoxy, alkenyl, alkynyl, amino, alkylthio, phosphino, silyl, —COR, —COOK, —PO$_3$R$_2$, —OPO$_3$R$_2$, and CN;
R$^2$ is aryl;
R$^6$ is selected from the group consisting of hydrogen, alkyl, aryl, alkylaryl, and arylalkyl;
R is the same or different at each occurrence and is independently selected from the group consisting of hydrogen, alkyl, aryl, alkenyl, and alkynyl; and
n is an integer from 0-3.

2. The device of claim 1, wherein said layer comprising a compound having Formula I further comprises an electroluminescent material.

3. The device of claim 1, wherein in Formula I, R$^6$ is selected from the group consisting of alkyl, aryl, alkoxyl, and aryloxy.

4. The device of claim 1, wherein in Formula I, R$^6$ is aryl.

5. The device of claim 1, wherein in Formula I, R$^6$ is selected from phenyl and naphthyl.

6. The device of claim 1, wherein in Formula I, R$^6$ is selected from arylalkyl, alkyl, and branched alkyl.

7. The device of claim 1, wherein in Formula I, R$^2$ is selected from phenyl and naphthyl.

8. The device of claim 1, wherein in Formula I, R$^1$, R$^3$, R$^4$, and R$^5$ are all hydrogen.

9. The device of claim 1, wherein in Formula I, R$^1$, R$^3$, R$^4$, and R$^5$ are independently selected from hydrogen, alkyl, alkoxy, and aryl.

10. The device of claim 1, wherein in Formula I, wherein n is 0 or 1.

11. The device of claim 1, wherein the compound of Formula I is selected from the group consisting of Compound H1 through H5: